(12) United States Patent
Toumazou et al.

(10) Patent No.: US 10,467,679 B1
(45) Date of Patent: Nov. 5, 2019

(54) PRODUCT RECOMMENDATION DEVICE AND METHOD

(71) Applicant: DNANUDGE LIMITED, London (GB)

(72) Inventors: Christofer Toumazou, London (GB); Maria Karvela, London (GB)

(73) Assignee: DNANUDGE LIMITED, London (GB)

( * ) Notice: Subject to any disclaimer, the term of this patent is extended or adjusted under 35 U.S.C. 154(b) by 0 days.

(21) Appl. No.: 16/384,049

(22) Filed: Apr. 15, 2019

(51) Int. Cl.
| | |
|---|---|
| G06Q 30/00 | (2012.01) |
| G06Q 30/06 | (2012.01) |
| G06F 1/16 | (2006.01) |
| A61B 5/00 | (2006.01) |

(52) U.S. Cl.
CPC ......... *G06Q 30/0631* (2013.01); *A61B 5/681* (2013.01); *G06F 1/163* (2013.01)

(58) Field of Classification Search
USPC ....................................................... 705/26.1
See application file for complete search history.

(56) References Cited

U.S. PATENT DOCUMENTS

| | | | |
|---|---|---|---|
| 3,885,383 A | 5/1975 | Tanaka | |
| 5,284,753 A | 2/1994 | Goodwin | |
| 5,478,989 A | 12/1995 | Shepley | |
| 5,935,858 A | 8/1999 | Herst | |
| 6,025,281 A | 2/2000 | Passlack et al. | |
| 6,587,022 B1 | 7/2003 | Devine | |
| 6,652,455 B1 | 11/2003 | Kocher | |
| 6,711,414 B1 | 3/2004 | Lightman | |
| 6,980,999 B1 | 12/2005 | Grana | |

(Continued)

FOREIGN PATENT DOCUMENTS

| | | |
|---|---|---|
| DE | 3508366 A1 | 12/1985 |
| EP | 0576998 A1 | 1/1994 |

(Continued)

OTHER PUBLICATIONS

Andrianova,M et al., Amplified Detection of the Aptamer-Vanillin Complex with the Use of Bsm DNA Polymerase, Sensors, 18, 49 available at www.mdpi.com/1424-8220/18/1/49 ,2018 ,1-13.

(Continued)

*Primary Examiner* — Mila Airapetian
(74) *Attorney, Agent, or Firm* — Saul Ewing Arnstein & Lehr LLP (57) ABSTRACT

A wearable device comprising: a memory configured to store product codes for consumable products and data indicating respective product recommendations or from which product recommendations can be derived; a product code reader for reading product codes from products; one or more inertial sensors for obtaining motion data for a wearer of the device; a visual indicator for providing a visual indication of a product recommendation, using data stored in the memory, in response to a read product code. The wearable device further comprises a processor configured to process the motion data to identify periods when the wearer is in a sitting position or other sedentary state, analyze the occurrence and durations of the periods, and modulate the recommendations accordingly for at least a subset of the product codes, whereby product recommendations change depending upon the identified periods.

17 Claims, 6 Drawing Sheets

(56) References Cited

U.S. PATENT DOCUMENTS

| | | | |
|---|---|---|---|
| 7,805,319 B2 | 9/2010 | Badinelli | |
| 7,851,207 B1 | 12/2010 | Sagripanti | |
| 8,386,519 B2 | 2/2013 | Kenedy et al. | |
| 8,630,448 B1 | 1/2014 | Shanmugam et al. | |
| 9,013,300 B2 | 4/2015 | Felix | |
| 9,414,623 B2 | 8/2016 | Minvielle | |
| 9,775,015 B1 | 9/2017 | Mishra et al. | |
| 9,858,799 B1 | 1/2018 | Deluca et al. | |
| 9,900,061 B1 | 2/2018 | Lui et al. | |
| 9,901,301 B2 | 2/2018 | Brenner et al. | |
| 2001/0051377 A1 | 12/2001 | Hammer et al. | |
| 2003/0005967 A1 | 1/2003 | Karp | |
| 2003/0134679 A1 | 7/2003 | Siegel et al. | |
| 2003/0162304 A1 | 8/2003 | Dority et al. | |
| 2003/0230606 A1 | 12/2003 | Devinie | |
| 2004/0018523 A1 | 1/2004 | Hawkins | |
| 2004/0103033 A1 | 5/2004 | Reade et al. | |
| 2004/0143447 A1 | 7/2004 | Lay | |
| 2005/0021679 A1 | 1/2005 | Lightman et al. | |
| 2008/0263011 A1 | 10/2008 | Badinelli | |
| 2010/0113892 A1 | 5/2010 | Kaput et al. | |
| 2010/0169340 A1 | 7/2010 | Kenedy et al. | |
| 2010/0312668 A1 | 12/2010 | Notsani | |
| 2011/0166881 A1 | 7/2011 | Brazzo et al. | |
| 2011/0220502 A1 | 9/2011 | Selden et al. | |
| 2011/0318717 A1 | 12/2011 | Adamowicz | |
| 2012/0005098 A1 | 1/2012 | Gross et al. | |
| 2012/0214159 A1 | 8/2012 | George | |
| 2013/0023058 A1 | 1/2013 | Toumazou et al. | |
| 2013/0096943 A1 | 4/2013 | Carey et al. | |
| 2013/0137169 A1 | 5/2013 | Kojima | |
| 2013/0262298 A1 | 10/2013 | Morley | |
| 2013/0275318 A1 | 10/2013 | Minvielle | |
| 2013/0337974 A1 | 12/2013 | Yanev et al. | |
| 2014/0085077 A1* | 3/2014 | Luna | G08B 6/00 340/539.11 |
| 2014/0090039 A1 | 3/2014 | Bhow | |
| 2014/0107932 A1 | 4/2014 | Luna | |
| 2014/0156295 A1 | 6/2014 | Cooper | |
| 2014/0214623 A1 | 7/2014 | Cancro et al. | |
| 2014/0277649 A1* | 9/2014 | Chong | G06N 20/00 700/94 |
| 2015/0044758 A1 | 2/2015 | Amshey et al. | |
| 2015/0073907 A1 | 3/2015 | Purves et al. | |
| 2015/0087478 A1* | 3/2015 | Zhang | A63B 24/0003 482/8 |
| 2015/0100445 A1 | 4/2015 | Johnson et al. | |
| 2015/0112857 A1 | 4/2015 | Gellis et al. | |
| 2015/0170249 A1 | 6/2015 | Cockcroft | |
| 2015/0227890 A1 | 8/2015 | Bednarek et al. | |
| 2015/0242837 A1 | 8/2015 | Yarbrough et al. | |
| 2015/0251074 A1* | 9/2015 | Ahmed | A61B 5/02405 700/91 |
| 2015/0317503 A1 | 11/2015 | Powell et al. | |
| 2015/0331946 A1 | 11/2015 | Balwani | |
| 2016/0004891 A1 | 1/2016 | Moon et al. | |
| 2016/0219124 A1 | 7/2016 | Elgrichi | |
| 2017/0061200 A1* | 3/2017 | Wexler | G06K 9/00255 |
| 2017/0098268 A1 | 4/2017 | Karvela et al. | |
| 2017/0166848 A1 | 6/2017 | Toumazou et al. | |
| 2017/0191060 A1 | 7/2017 | Jackson | |
| 2017/0242963 A1 | 8/2017 | Cohen et al. | |
| 2017/0323057 A1 | 11/2017 | Karvela et al. | |
| 2018/0053242 A1 | 2/2018 | Agrawal | |
| 2018/0095429 A1* | 4/2018 | Weinstein | G06Q 10/06311 |
| 2018/0140203 A1 | 5/2018 | Wang et al. | |
| 2018/0182253 A1* | 6/2018 | Hor-Lao | G09B 5/02 |
| 2018/0236242 A1 | 8/2018 | Balinski et al. | |
| 2018/0374567 A1* | 12/2018 | Toumazou | G06Q 30/0269 |

FOREIGN PATENT DOCUMENTS

| | | |
|---|---|---|
| EP | 1329835 A1 | 7/2003 |
| EP | 2733579 A2 | 1/2019 |
| GB | 2509481 A | 7/2014 |
| WO | 03027236 A2 | 4/2003 |
| WO | 2005027716 A2 | 3/2005 |
| WO | 2006086669 A2 | 8/2006 |
| WO | 2008019695 A2 | 2/2008 |
| WO | 2008107014 A1 | 9/2008 |
| WO | 2013008042 A1 | 1/2013 |
| WO | 2014008381 A2 | 1/2014 |
| WO | 2014022907 A1 | 2/2014 |
| WO | 2015054034 A1 | 4/2015 |
| WO | 2016019476 A1 | 2/2016 |
| WO | 2016117726 A1 | 7/2016 |
| WO | 2016170445 A2 | 10/2016 |
| WO | 2017055867 A1 | 4/2017 |

OTHER PUBLICATIONS

Guo, X et al., Development of an Ultrasensitive Aptrasensor for the Detection of Aflatoxin B1, Biosensors * Bioelectornics, vol. 56, 2014, 340-344.

Li, F. et al., Aptamers Facilitating Amplified Detection of Biomolecules, Analytical CHemistra, vol. 87, 2015, 274-292.

Ma, et al., Femtogram Ultrasensitive Aptasensor for the Detection of Ochratoxin A, Biosensors & Bioelectronics, vol. 42, 2013, 545-549.

Spurgeon, Sandra et al., High Throughput Gene Expression Measurement with Real Time PCR in a Microfluidic Dynamic Array, PLoS ONE, vol. 3, Issue 2, e1662, Feb. 2008, 1-7.

Cavallo, "Links Between DNA-Based diet and Salivary Leptin Hormone Concentration," 2018 IEEE Biomedical Circuits and Systems Conference, pp. 1-4 (Oct. 1, 2018) XP055566582.

Liao et al., Aptamer-Based Sensitive Detection of Target Molecules via RT-PCT Signal Amplification, Bioconjugate Chem., 21, pp. 2183-2189 (2010).

Kuznetsov et al., "Aptamer based vanillin sensor using an ion-sensitive field-effect transistor," Microchimica Acta, 18S:3, https://doi.org/10.1007/s00604-017-2586-4 (2018).

Sassolas et al., "Homogeneous assays using aptamers," Analyst, 136, pp. 257-274 (2011).

Wang et al., "A Gold Nanoparticle-Based Aptamer Target Binding Readout for ATP Assay," Advanced Materials, 19, pp. 3943-3946 (2007).

* cited by examiner

PRODUCT RECOMMENDATION DEVICE AND METHOD

TECHNICAL FIELD OF THE INVENTION

The present invention relates to a wearable device and a method for providing recommendations of consumable products.

BACKGROUND OF THE INVENTION

Personal activity monitors provide users with a convenient way of recording their physical activity. In particular, many so-called "fitness trackers" provide users with estimates of the distance they have walked or run, or the total energy they have expended and so forth. This kind of data allows users to make more informed decisions regarding their lifestyle. In some cases, a fitness tracker may remind the user to perform that they have not undertaken moderate or vigorous physical activity recently. While such fitness trackers may help individuals improve their health by motivating them to undertake more physical activity, other factors such as the food and drink the user consumes also play an important role in determining the wellbeing of the individual.

US2018/0374567A1 describes a wrist-worn barcode scanner for providing product recommendations to a user based on his or her personal biological information. The scanner includes sensors for measuring various physiological or biochemical functions of the user, such as his or her calorific expenditure or heart rate. The data obtained by the sensors is used to adjust the product recommendations. For example, if the data indicates that the user has not undertaken enough physical exercise then products with a high calorific content are no longer recommended.

SUMMARY OF THE INVENTION

According to a first aspect of the invention there is provided a wearable device comprising: a memory configured to store product codes for consumable products and data indicating respective product recommendations or from which product recommendations can be derived; a product code reader for reading product codes from products; one or more inertial sensors for obtaining motion data for a wearer of the device; a visual indicator for providing a visual indication of a product recommendation, using data stored in the memory, in response to a read product code; and a processor configured to process the motion data to identify periods when the wearer is in a sitting position or other sedentary state, analyse the occurrence and durations of said periods, and modulate said recommendations accordingly for at least a subset of said product codes, whereby product recommendations change depending upon the identified periods.

Consumable products as referred to in this document are edible or drinkable products, such as food or beverages.

The processor may be configured to modulate recommendations according to the wearer's behaviour determined by the processor for a pre-determined period, such as the same day.

The processor may be configured to identify and maintain a count of periods when the wearer is in a sitting position or other sedentary state for a duration longer than a threshold duration, such as 10 minutes, 30 minutes or 60 minutes.

The processor may be configured to ignore interruptions in which the user is not in a sitting position or other sedentary state for less than a pre-determined time when identifying said periods.

The memory may store nutritional data for each product and the processor may be configured to select the subset of product codes based on the nutritional data.

Each product recommendation may have a first, recommended state and a second, not recommended state and the modulation changes a product recommendation between the first and the second state.

The product recommendation may have a first, recommended state, a second "maybe recommended" state and a third, not recommended state and the modulation changes the product recommendation between the first and the second state.

The wearable device may be a wrist-worn wearable device.

The one or more inertial sensors may comprise an accelerometer and/or a gyroscope.

The product code reader may be for reading a one-dimensional or two-dimensional barcode.

The visual indicator may provide the indications of the product recommendations by means of different coloured illuminations, for example red and green, or red, green and amber.

According to a second aspect of the invention, there is provided a method of providing recommendations in respect of consumable products to a wearer of a wearable device in order to improve the wearer's health. The method comprises: storing, in a memory of the wearable device, product codes for products and data indicating respective product recommendations or from which product recommendations can be derived; obtaining, from one or more inertial sensors of the wearable device, motion data for the wearer; processing the motion data using a processor of the wearable device to identify periods when the wearer is in a sitting position or other sedentary state; analysing the occurrence and durations of said periods using said processor; reading a product code from a product using a product code reader of the wearable device; in response to a read product code, using data stored in said memory to obtain a product recommendation; modulating said product recommendation depending upon the wearer's sitting behaviour, or sedentary behaviour, determined by the processor; and providing a visual indication of the modulated product recommendation using a visual indicator of the wearable device.

The method may further comprise selecting a subset of product codes for which the associated product recommendations are modulated.

Selecting a subset of product codes for which product recommendations are modulated may comprise selecting products codes based on nutritional information for the associated products.

Selecting products codes based on nutritional information for the associated products may comprise ranking the products based on the respective nutritional information for each product and selecting the subset by selecting products having a ranking higher than a pre-determined ranking.

The nutritional information may comprise one or more of: calorific content, sugar content, carbohydrate content, saturated and/or unsaturated fat content, and salt content, The data may be derived from personalised data derived from personalised biological information obtained from an analysis of a biological sample provided by the wearer of the device.

According to a third aspect of the present invention, there is provided a method of providing product recommendations in respect of consumable products in order to benefit the health of a user. The method comprises: identifying one or more health traits of the user; for each of a multiplicity of consumable products, calculating a score indicative of how the product affects each of said health traits, each score being based at least partly on nutritional information for the product; assigning a product recommendation to each product based on said scores; monitoring the behaviour of the user by identifying periods when the user is in a sitting position or other sedentary state; based on said behaviour of the user, modulating the product recommendation for at least of a subset of said products; and providing the modulated product recommendation to the user via a visual indicator.

The product recommendation for each product may be stored in a database installed in a memory of a wearable device, said memory further storing data indicative of whether the product belongs to said subset.

The wearable device may comprise one or more inertial sensors for identifying periods when the user in a sitting position or other sedentary position.

DETAILED DESCRIPTION OF THE INVENTION

Whilst a lack of physical activity has long been recognised as detrimental to health, the negative effects of sitting are generally underappreciated. Ekeland et al., The Lancet 2016, 1303-1310 (388), identifies that sitting is critical to health and recommends that three times the recommended daily activity is required to compensate for extended periods of sitting. However, it is not always possible for users to undertake the recommended amount of daily activity, let alone three times the recommended daily activity. Considering a wearable product recommendation device such as that described in US2018/0374567A1, configuring the device so as to adjust product recommendations according to the device wearer's sitting behaviour may go some way to mitigating for extended periods of sitting. Additionally, for many users, a clear and visible indication that certain products are no longer recommended because they have been sitting for too long, may in itself act as a motivator to avoid prolonged periods of sitting and to engage in physical activity.

The device and method presented here flow from a realisation that an individual's health can be improved by using a wearable computer device to provide product recommendations that are modulated depending upon the individual's sitting behaviour as detected by the device.

Figure 1:
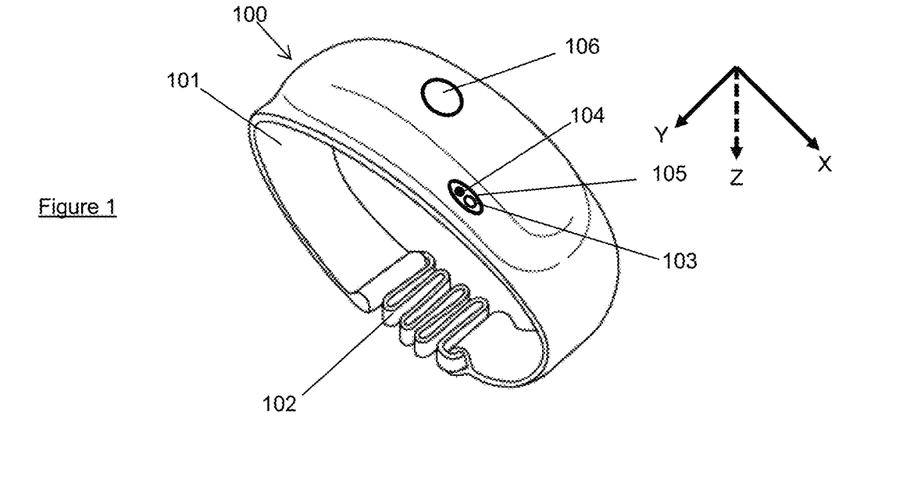
FIG. 1 is a perspective schematic view of a wearable device according to an embodiment of the invention.

FIG. 1 illustrates a wearable device 100 (or "wristband") comprising a strap 101, which in this example has an expandable section 102 to allow the user to slide the wristband 100 easily over his or her wrist. In other examples, a wrist strap, such as those found on wristwatches, may be used in place of the strap with expandable section. FIG. 1 also shows three orthogonal axes X, Y and Z used to describe the orientation of the wristband 100. The Y axis is oriented in along the axis of the wristband, i.e. the direction in which the wearer's wrist passes through the wristband 100. The X and Z axes are perpendicular to the Y axis (and to one another), with the Z-axis aligned from top to bottom of the wristband 100, i.e. the Z axis points from the outside to the inside of the wrist when the wristband 100 is worn with the expandable section 102 on the inside of the wrist.

Figure 2:
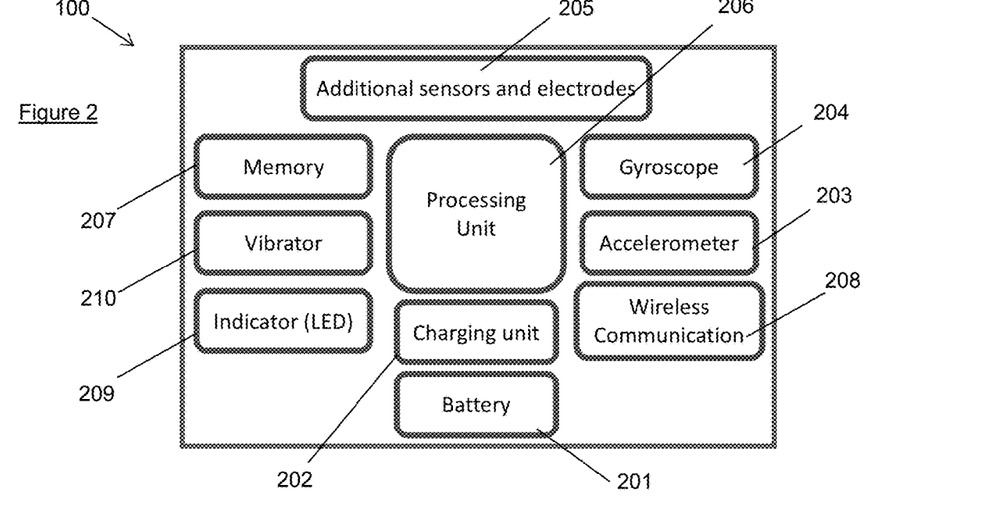
FIG. 2 is a schematic system view of the wearable device of FIG. 1.

The wristband 100 comprises an optical sensor 103, such as a photovoltaic cell or camera, and a light source 104, such as a laser. A window 105 is provided in the wristband 100 to allow the optical sensor 103 to be used for reading product codes and the light source 104 to be used to illuminate the product code. An indicator (or indicators), such as a light emitting diode (LED) 106, is also provided in order to give feedback to the wearer about a product. The cross section of the strap 101 is thicker on one side in order to accommodate the various components of the wearable device 100 (see below). FIG. 2 shows a schematic system view of wristband 100.

The wristband 100 is powered by a battery 201, which can be charged using a charging unit 202, and has inertial sensors for measuring the motion of the wristband 100 in 3D space, an accelerometer 203 (e.g. a tri-axial accelerometer) and/or a gyroscope 204. The axes of the accelerometer 203 and/or gyroscope 204 are aligned with respect to the three orthogonal axes X, Y and Z shown in FIG. 1.

The wristband 100 may also comprise additional sensors and electrodes 205, such as a heart monitor (e.g. an electrocardiogram, ECG) or thermometer for measuring the user's heart rate or temperature, and/or a GPS sensor for tracking the user's location. Sensors may include, for example, a microphone or optical sensor for measuring heart rate.

The wristband 100 is controlled by a processing unit 206 which accesses instructions and data stored in a memory 207. A wireless communication module 208 is provided to allow the processing unit 206 to communicate with other computer devices such as other wristbands, smartphones, smartwatches or personal computers. The wireless communication module 208 can be used, for example, to provide or update a database of product codes and/or product recommendations stored in memory 207. The wireless communication module 208 may allow data to be exchanged between wristbands 100.

The wearer may activate the light source 104 and direct light onto a product in order to read a product code (or other information) from the product using the optical sensor 103. The wearer may manipulate or hold the product using either one of their hands, or both of their hands together, in order to orient the product correctly for reading. Alternatively, the wearer may move or orient the wristband 100 in order to read the product code whilst the product remains in place on a supermarket shelf (for example). After reading the product code, the wristband may provide feedback to the wearer using the indicator (LED) 109, which may be an RGB LED which can be adjusted to show different colours by mixing different combinations of the RGB components and/or adjusting the brightness and/or blinking pattern of the LED. Of course, other types of indicator can also be used, such as LED arrays or screens such as LCD, LED or OLED screens.

Examples of the other sensors which may be incorporated into the wearable device are:
- Pedometers/step counters;
- Pulse rate sensors, e.g. photoplethysmography (PPG) sensors;
- Respiration rate sensors;
- Heart rate sensors (also for measuring heart rate variability);
- Blood pressure sensors;

Various steps in controlling how the wearable device 100 provides product recommendations to the wearer will now be described.

Figure 3:
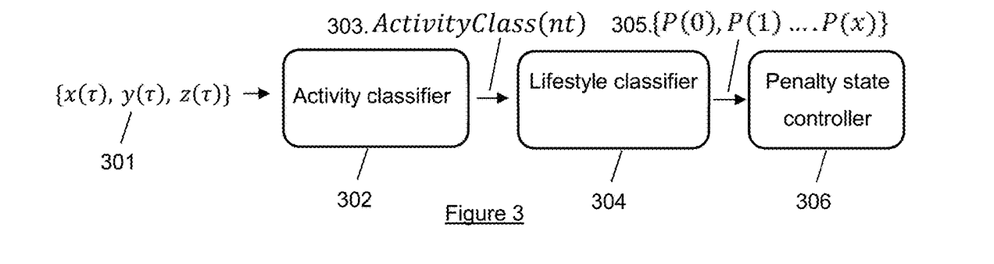
FIG. 3 is a flow diagram of the data processing performed by the wearable device of FIG. 1.

FIG. 3 shows how the motion data 301 collected by the inertial sensors 203, 204 is processed to update the product recommendations. In this example, the motion data 301 includes acceleration components (x, y, and z) along three orthogonal directions of the wearable device 100 in 3D space, measured at a series of time steps (i) by the tri-axial accelerometer 203. The motion data 301 may also include data derived from the acceleration components such as the position or velocity of the wearable device 100. The motion data 301 may also include the orientation (or the angular velocity or angular acceleration) of the device in 3D space, as determined by the gyroscope 204, for example.

The motion data 301 is provided to an activity classifier 302, typically at a sampling rate of 40 Hz. As described in more detail below with reference to FIGS. 4A and 4B, the activity classifier 302 processes the motion data 301 to determine an activity class for the wearer of the device, such as sitting, inactive, active or unknown. The activity class can be updated when each sample of the motion data 301 is received or, more commonly, after a threshold number of samples of motion data 301 is received, such that the activity class is updated with a lower frequency than the sampling rate.

The activity classifier 302 provides activity class data 303 to a lifestyle classifier 304, typically at a sampling rate of 1 Hz. As described in more detail below with reference to FIG. 5, the lifestyle classifier 304 accumulates the activity class data 303 and determines from the data a list of accrued penalties 305 according to the behaviour of the device wearer. Penalties are accumulated over a period of 24 hours, for example.

The lifestyle classifier 304 provides the list of penalties 305 to a penalty state controller 306, typically on a daily basis, although a shorter interval (e.g. hourly) or a longer interval (e.g. weekly) could also be used. As described in more detail below with reference to FIG. 6, the penalty state classifier 306 determines a penalty state for the wearable device 100 based on the list of penalties 305. The penalty state may also be based on other factors, such as information about the wearer, e.g. their age, sex or product purchase history (which in some embodiments is measured using the wearable device 100). When the penalty state controller 306 determines that the device 100 should be placed in a penalty state, it sets a flag in the memory 207 to indicate that the device 100 should provide adjusted product recommendations. If no penalty state is determined then the flag may be unset such that the device 100 provides product recommendations which are not affected by the wearer's sitting behaviour.

Figure 4A:
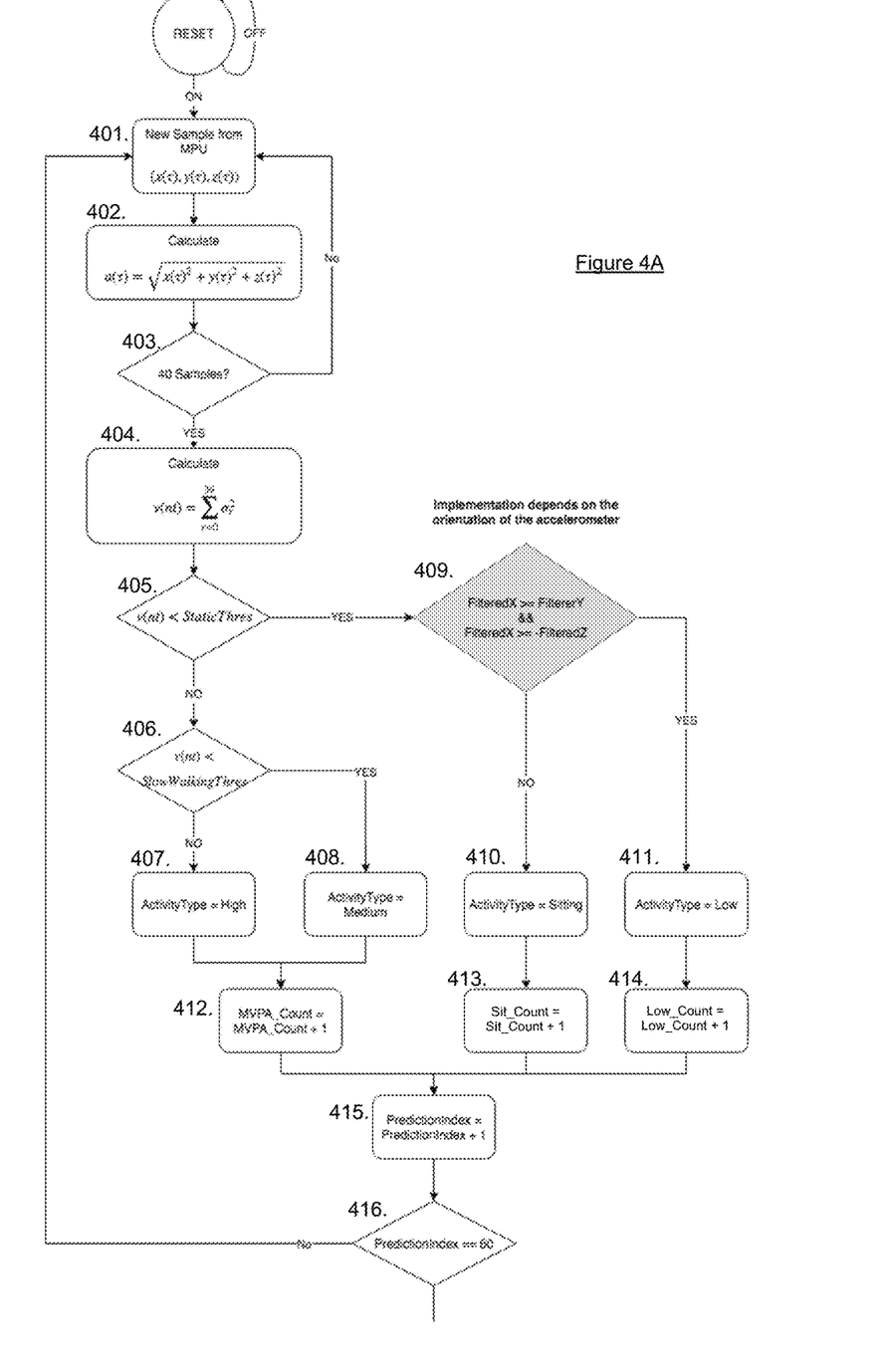
FIGS. 4A and 4B are a flow diagram of the data processing performed by the activity classifier of FIG. 3 (FIG. 4B is a continuation of FIG. 4A)

FIG. 4A shows how the motion data 301 obtained from the inertial sensors (referred to in this figure a Motion Processing Unit, MPU) is processed by the activity classifier 302. Once the wearable device 100 is turned on, the activity classifier 302 begins to receive samples 401 from the MPU. Each time a sample is received, the magnitude (e.g. Euclidean norm) of the acceleration is calculated from the x, y and z components of the acceleration measured by the accelerometer 203. After a threshold number of samples have been received 403 (in this case, 40 samples), the variance of the acceleration is calculated 404 for the samples. The variance is then compared to a threshold 405 to determine whether or not the device wearer is relatively static. If the threshold is exceeded then a further comparison is made to determine if the variance exceeds another threshold associated with the variance expected for slowly walking. If this latter threshold is exceeded then the activity type is classified as "High" 407; if not, the activity type is classified as "Medium".

Returning to the comparison of the variance of the acceleration with the threshold for static behaviour 405, if the variance is less than this threshold, the sample data is filtered and processed 409 to determine whether or not the device wearer is sitting. The filtering removes unwanted noise from each x, y and z component of the acceleration, e.g. using a band-pass filter. The filtered acceleration components can be used in a number of ways to determine whether the wearer of the device is sitting. For example, the contribution of the acceleration due to gravity in the filtered acceleration components can be used to determine the lower arm posture of the wristband wearer (assuming that the wristband is worn in a conventional way), and hence whether the wearer is performing a low level of activity while standing or sitting. In the exemplary formula shown in element 409 of the figure, the filtered components are compared with each other to identify whether the acceleration of the device 100 along one of the axes (in this case the X direction) is greater than the acceleration along each of the two other axes, as this is typically correlated with the wearer performing a low level of activity while standing/not sitting, e.g. the wearer swinging his or her arms backwards and forwards while walking. The details of how such a comparison is implemented depend on the orientation of the accelerometer 203. A gyroscope 204 may be used in conjunction with the accelerometer 203 to improve sitting detection accuracy. Other methods for detecting sitting which can be used include machine learning methods in which a classifier is trained based on motion data which has been labelled according to the type of activity performed by the wearer of the device as a function of time. As a result of this analysis, the activity type for the period covered by the samples of motion data is determined to be either sitting 410 or low 411.

After the activity type has been determined, one of three counters is incremented depending on the activity type. If the activity type is "high" or "medium" then a counter for Moderate to Vigorous Physical Activity (MVPA) is incremented 412, whilst if the activity type is "sitting" or "low" then respective counters for sitting 413 and low 414 may be incremented. Regardless of the activity type, a counter for a prediction index is incremented 415 in order to count the number of times the activity type has been predicted. If the prediction index does not exceed a threshold, in this case 60 iterations, the activity classifier 302 waits for further samples to be received from the inertial sensors (MPU) 401 and the process is repeated. The threshold is chosen such that a reliable prediction of the wearer's behaviour can be obtained.

Figure 4B:
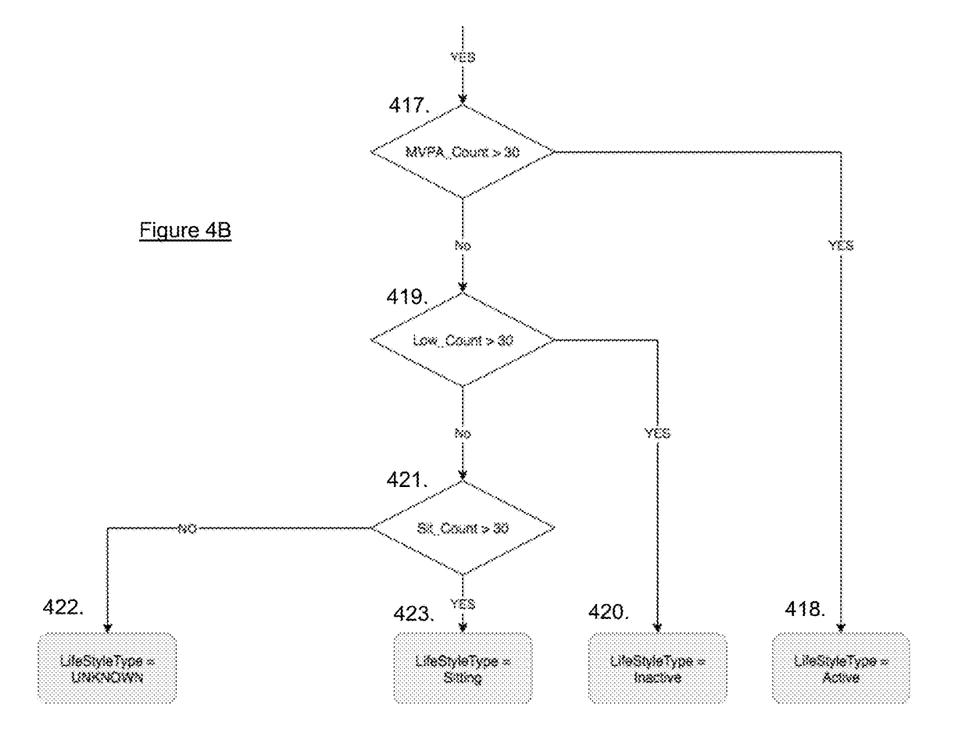

FIG. 4B is a continuation of FIG. 4A and shows the process performed by the activity classifier 302 after the prediction index has been found to exceed the threshold, i.e. after a sufficient number of activity type classifications have been performed. A determination is made of whether the MVPA counter is above a certain value (in this case, 30 counts) 417 and, if so, the lifestyle type associated with the samples of motion data 301 is set as "active" 418. Otherwise, a determination is made of whether the low counter is above a certain value (in this case, 30) 419 is made and, if so, the lifestyle type is set as "inactive" 420. Otherwise, a determination is made of whether the sit counter is above a certain value (in this case, 30) 421: if it is, then the lifestyle type is set as "sitting", or if not, the lifestyle type is set as "unknown". In other words, the final stages of the process 417-423 determine the predominant behaviour of the device wearer over the relevant period, i.e. whether the user has been active or sitting for more than half the time. After this has been done, the counters are each reset and the process of FIGS. 4A and 4B is repeated.

Figure 5:
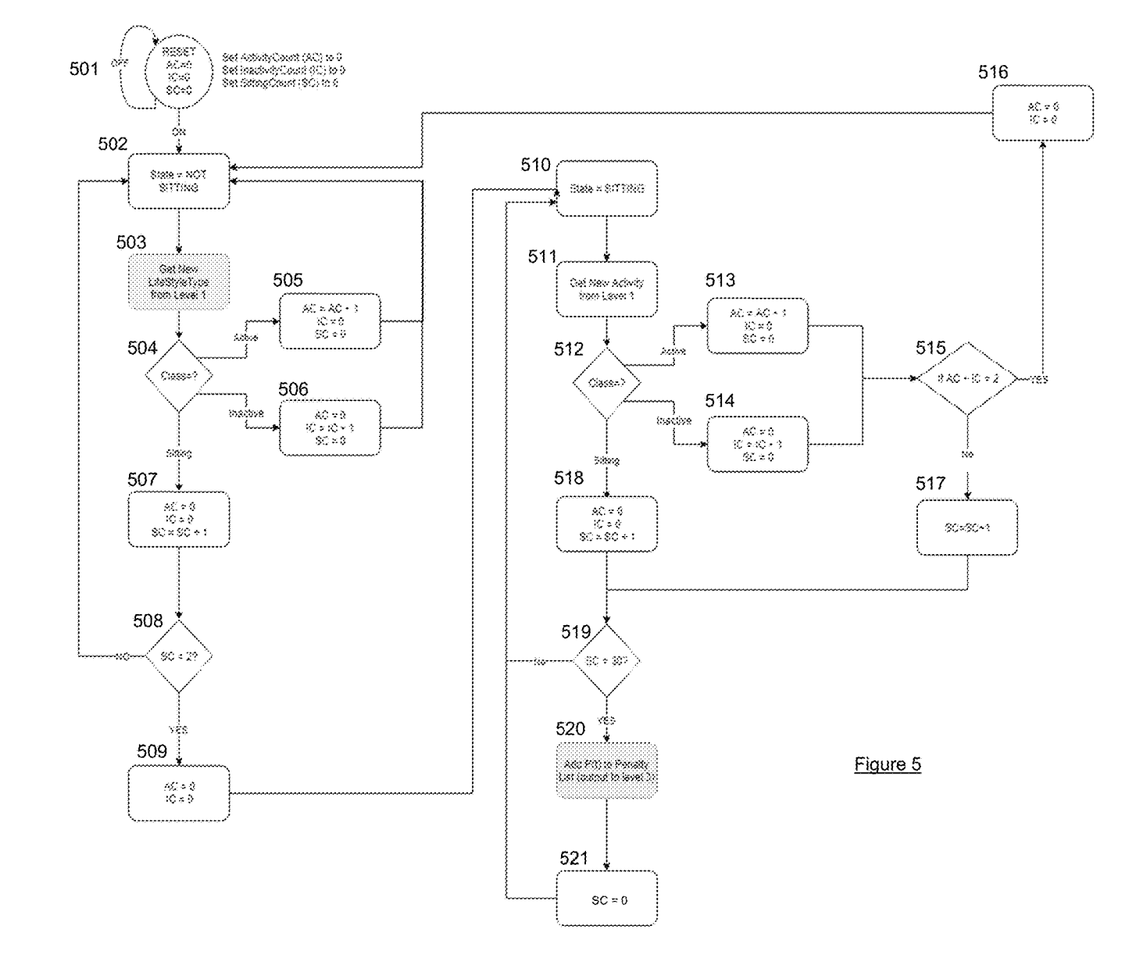
FIG. 5 is a flow diagram of the data processing performed by the lifestyle classifier of FIG. 3.

FIG. 5 shows how the lifestyle classifier 304 processes the lifestyle types obtained from the activity classifier 302. The lifestyle classifier 304 has counters for activity (AC), inactivity (IC) or sitting (SC) which are initially set to zero 501. The initial state of the classifier 304 is set to be "NOT SITTING". On receipt of a lifestyle type from the activity classifier 302 (referred to here as "Level 1") 503, the lifestyle classifier 304 determines the type and increments the respective counter, whilst setting the other counters to zero 505, 506 and 507. For example, when the activity counter is incremented then the inactivity and sitting counters are set to zero 505. After incrementing the activity counter or the inactivity counter the state of the classifier 304 remains "NOT SITTING" and the process 502-504 is repeated for the next lifestyle type determined from the motion data 301. If the sitting counter is incremented 507 then a determination of whether the sitting counter has reached a particular value 508 (in this case, 2 counts). In other words, steps 504 to 508 determine whether the device wearer has been sitting continuously for a certain period (2 cycles), i.e. without their sitting being interrupted by a period of MVPA or low-level non-sitting activity. If this criterion 508 has not been met, the state of the classifier 302 remains "NOT SITTING" and the process is repeated again. However, if the criterion 508 has been met, then the activity and inactivity counters are set to zero 509 and the state of the classifier 304 is set to "SITTING".

Once the lifestyle classifier 304 enters the "SITTING" state 510, it continues to receive lifestyle types from the activity classifier 302. The lifestyle classifier 304 processes the lifestyle types 511, 513 in a similar way as when it is in the "NOT SITTING" state. However, after either of the activity 513 and inactivity 514 counters is incremented (and the other counters set to zero) a determination is made of whether the either of the activity and inactivity counters exceeds a certain value (in this case, 2 counts). In other words, the classifier 304 determines whether the device wearer has undertaken MVPA continuously for the last two cycles or low-level non-sitting activity continuously for the last two cycles. If they have, then the activity and inactivity counters are reset to zero 516 and the state of the classifier 304 is returned to "NOT SITTING" 502. If not, then the sitting counter is incremented 517.

After the sitting counter is incremented, either at step 517 or 518, a determination is made of whether the sitting count exceeds a threshold 520 (in this case, 30 counts). If it does, a penalty is added to the penalty list 520 and the sitting counter is set to zero 521. The process then restarts 510 with the state of the classifier 304 remaining as "SITTING".

Figure 6:
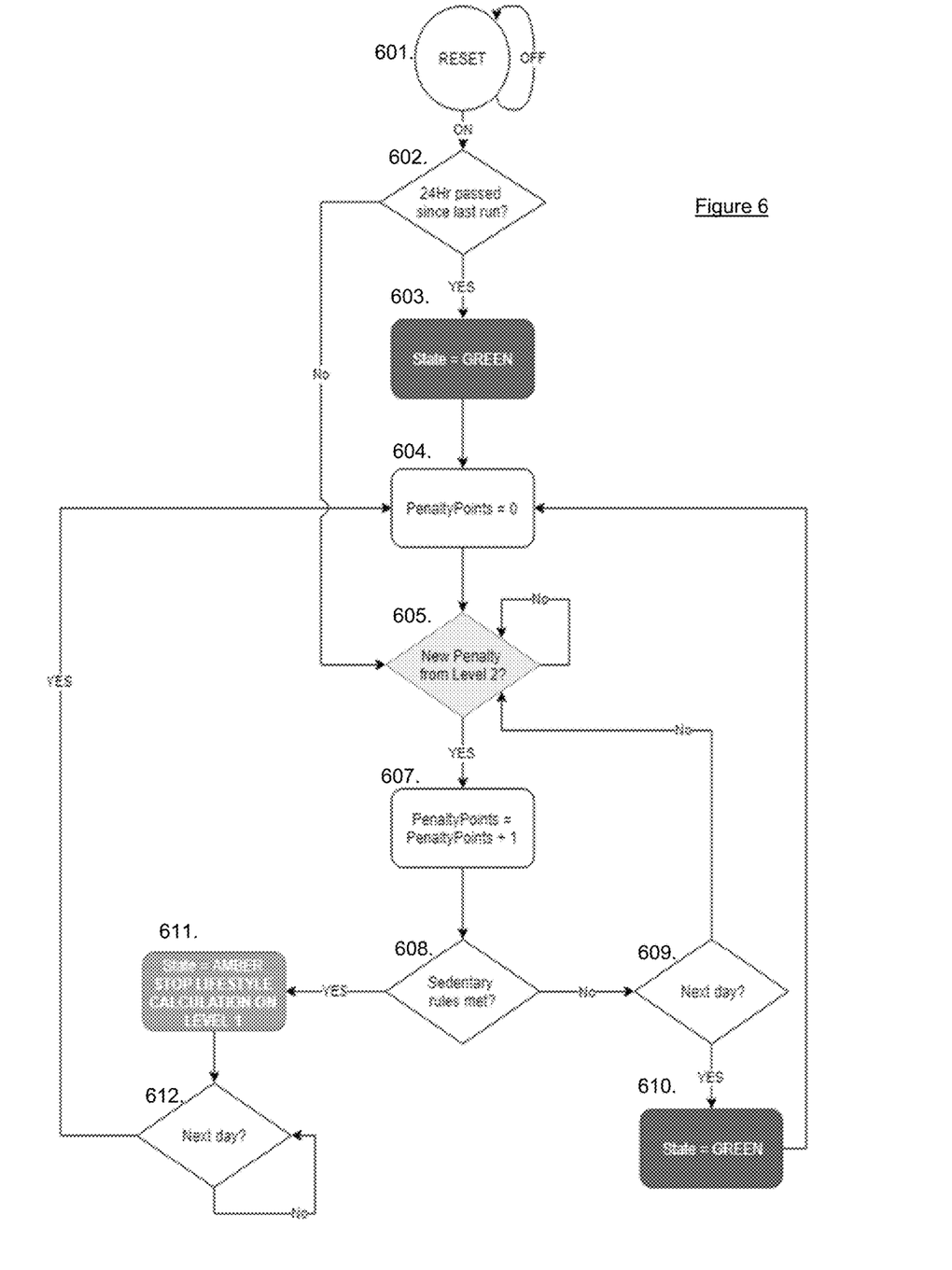
FIG. 6 is a flow diagram of the data processing performed by the penalty state controller of FIG. 3.

FIG. 6 shows how the penalty state controller 306 uses the penalty list to control the behaviour of the wearable device 100. When the device 100 is turned on or reset 601, the controller 306 determines whether a certain period (in this case, 24 hours) has elapsed since the wearable device was last operational. If it has, then the state of the controller 306 is set to "GREEN" and a penalty score is also set to zero 604. In the "GREEN" state, the product recommendations are not modulated when the device 100 is used to read a product code, but rather the "normal" product recommendations (e.g. product recommendations based on the genotype of the user) are indicated to the user.

The controller 306 waits 605 to receive a new penalty from the lifestyle classifier 304. When a penalty is received, the penalty score is incremented 607 and a determination is made 608 of whether so-called "sedentary" rules have been met. These rules may differ according to user information, such as whether the user is a child or adult. For example, a rule for an adult may state that if there a penalty score of 12 or more in a 16 hour period then the user is classified as "sedentary", whilst for the corresponding rule for a child may require a penalty score of only 6 or more. If the sedentary rules are not met 609, then a check is made whether a new day has started 609 (or some other period has elapsed) and, if not, the controller 306 continues to wait 605 for a further penalty point to be received from the lifestyle classifier 304. If a new day has started, the state of the controller remains "GREEN" 610 and the penalty score is set to zero 604, as previously.

A failure to meet the sedentary rules (or rule) causes the state of the controller 306 to become "AMBER" 611. In this state, the product recommendations provided by the device 100 are modulated. The controller 306 remains in this state until the next day 612, after which the penalty score is set to zero once more 604 and the state is set back to "GREEN" (not shown).

In one example, the product recommendations may of three different types: not recommended, maybe recommended and recommended. These types may be indicated to the user using the colour-changing LED 106 of the device 100. For example, a traffic light system of red (not recommended), amber (maybe recommended) and green (recommended) can be used. When the controller 306 is in the "GREEN" state, then "normal" product recommendations are provided to the user. However, if too many penalty points have been accrued and the controller 306 enters the "AMBER" state, a subset of the product recommendations which would otherwise have been indicated using the green light may be indicated to the user with an amber light. For example, a food product with a moderately high calorie content may usually be recommended as being suitable for a particular user (i.e. indicated with a green light). However, if the user has been sitting for a prolonged period, the product recommendation may be adjusted (modulated) to "maybe recommended" (i.e. indicated with an amber light).

The controller 306 can also be configured so that a subset of products which are normally "maybe recommended" (i.e. indicated with an amber light) become "not recommended" (i.e. indicated with a red light) based on the sitting behaviour of the device wearer, as described above. However, products which are "not recommended" are, in general, not affected by sitting behaviour (i.e. always indicated with a red light).

The use of three "states" of product recommendation described above is provided by way of example only. It is of course possible to use only two product recommendation states ("recommended" or "not recommended") or to use more than three product recommendation states, e.g. a recommendation score, which may be out of 100, for example or may be positive or negative, with negative values indicating that a product is not recommended and vice versa. Where a recommendation score is used, the modulation may be applied by decreasing the score based on the number of penalty points accrued by the wearer.

The subset of products for which the recommendation is modulated by sitting behaviour may be chosen in a number of ways. In general, the modulation is not applied to all types of food product because to do so may cause "healthy" products such as vegetables to be "maybe recommended" based on the user's sitting behaviour. The subset may be chosen based on nutritional data associated with each product. In one example, the products which are classified as being "recommended" are ranked according to their calorific content and the top 50%, 30% or 10% of the products with the highest calorific content are selected for modulation. In some embodiments, the cut-off percentage for selecting the products this way can be adjusted by the user in order to increase or decrease the number of products for which the modulation is applied.

In general, the following procedure may be used to obtaining product recommendations. Firstly, a number of health traits associated with potentially poor health are identified, including for example, type-II diabetes, hypertension, high body mass index (BMI), and high cholesterol. Whether or not a user has any of the these health traits may be determined using genetic testing e.g. based on detecting single nucleotide polymorphisms (SNPs) in a sample of the user's DNA, although other forms of diagnostic testing can also be employed, such as testing the user's breath to determine the composition of their microbiome.

Once the "target" health traits have been identified, the effect of diet on each of them is considered. This is done by analysing how the health trait is likely to be affected for each of a number of different categories relating to the nutritional content of consumable products, including any of the following, for example: sugar content, calorific content, carbohydrate content, saturated fat content, total fat content, and salt content. For example, it is known that the risk of type-II diabetes can be raised by consumption of products which are high in sugar, whilst salt-rich diets are linked to hypertension. The relationship between each category and each health trait can be quantified by assigning a trait-dependent coefficient to each of the categories. Taking hypertension as an example, large coefficients may be assigned to salt content and fat content, whilst small (or even zero) coefficients may be assigned to calorific content and carbohydrate content.

For each identified health trait, the trait-dependent coefficients can be used to calculate a score which indicates the expected effect of a product based on its nutritional content, i.e. how many grams of salt, saturated fat, etc the product contains. For example, to calculate a score which is indicative of the adverse effect of a product on hypertension, the number of grams of salt in the product can be multiplied by the coefficient for salt content. Mathematically speaking, the score for each trait may be determined by taking a scalar product of a vector of the trait-dependent coefficients with a vector of nutritional information for each product. Of course, more sophisticated ways of calculating the scores can also be used, such as using a dose-response curve determined for a health trait to model the likely effect of the different types of nutritional category on that trait. The score may also take into account other factors, such as the type of product (e.g. confectionary, biscuits, breakfast cereals etc.) and the typical portion size for the products. These other factors may be used to adjust the scores for differences in how different products are consumed, e.g. if a product is identified as typically being consumed as a "treat" then its score may be reduced so that its recommendation may be more positive than it would otherwise have been.

After the scores have been calculated for each product, the products are ranked in descending order according to their score for a particular health trait. A subset of the products is then chosen by selecting products which have a ranking which is higher than a threshold ranking, e.g. products which are in the top 50% or 30% or 10% of products based on their score of the health trait. These products may be assigned a "negative" recommendation, such as "not recommended", so that when the wristband 100 is used to read the barcode of the product, the LED 104 turns red (for example). The remaining products are assigned to a different category, e.g. "recommended" (which would be indicated to the user with a green colour). Thus, the products are allocated different recommendations according to their ranking for a particular trait. The value of the threshold ranking or "cut off" which is used for allocating the recommendations varies from user to user and is determined based on how susceptible the user is to the particular trait (as determined by genetic testing, for example).

The potential effects of sitting (or other forms of sedentary behaviour) are accounted for by selecting a further subset of products for which the associated product recommendations are modulated depending on the penalty state of the controller 306. This subset may be determined by selecting products which are below the threshold ranking mentioned above, but above a second threshold ranking. For example, if 50% of the products are "recommended" for a particular trait, then the top 20% of these products may be chosen for the subset which is to be modulated. The second threshold ranking is chosen based on how severely the particular health trait is affected by sitting and/or other types of sedentary behaviour. The subset of products may be assigned to a particular database table or otherwise "flagged" in the memory of the wristband 100 so that it can be easily determined whether the product recommendation for a particular product should be modulated. In one example, if the controller 306 is in the "AMBER" state, the products in the subset are indicated as being "maybe recommended" (e.g. the indicator turns amber) whereas if the controller 306 is in the "GREEN" state, they are "recommended" (e.g. the indicator turns green).

The product recommendations for each health trait are combined to determine an overall product recommendation for each product. This can be done in a number of ways, such as determining that the product is "not recommended" if the product is "not recommended" for any of the traits or, alternatively, if the product is "not recommended" for more than one of the traits. The flag indicating whether the product recommendations should be modulated can also be set or unset for each product based on the same or similar kinds of rule.

In general, the threshold rankings mentioned above, and the rules for determining the overall product recommendations, strike a balance between allowing users to choose products they wish to consume and dissuading them from consuming at least some of the products which are most likely to have a negative impact on their health. This balance is advantageous because the user is "nudged" into making choices which are better for him or her in the long term. Modulating the product recommendations based on the user's sitting and/or other sedentary behaviour provides an additional "nudge" so that, for example, a user may notice that a product which is normally "recommended" is only "maybe recommended" (or recommended as being "discretionary"), if the user has been sitting for long periods during a particular day. Using a modulation which does not make the products "not recommended" may be particularly advantageous because it does not penalise the user too harshly for circumstances which may be out of their control, e.g. if the user has been sitting for a long time because they have had to travel a large distance.

Figure 7:
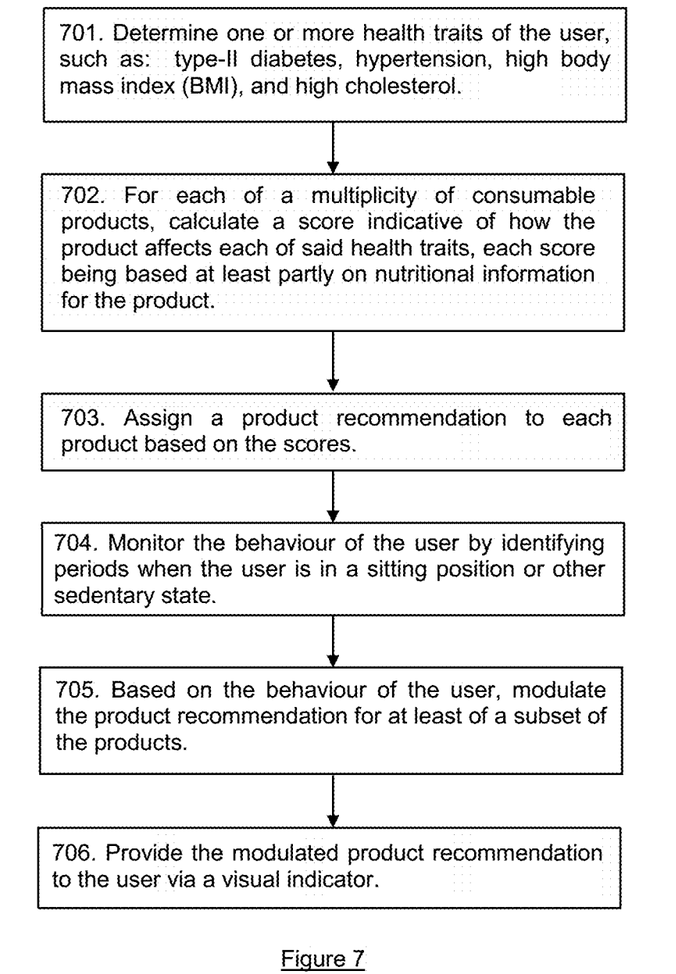
FIG. 7 is a flow diagram of a method of providing product recommendations to a user.

FIG. 7 provides an overview of the steps involved in a method of providing a user with product recommendations. The steps of the method are as follows:

Step 701: Determine one or more health traits of the user, such as: type-II diabetes, hypertension, high body mass index (BMI), and high cholesterol, e.g. by performing a genetic test on a biological sample provided by the user.

Step 702: For each of a multiplicity of consumable products, calculate a score indicative of how the product affects each of said health traits, each score being based at least partly on nutritional information for the product. The scores may be calculated using the procedure described above, e.g. for each product, determining its nutritional content each of a number of categories (e.g. using product nutritional information provided by the manufacturer of the product), multiplying the nutritional content in each category by a trait-dependent coefficient and summing the resulting values to produce an overall score for each trait.

Step 703: Assign a product recommendation to each product based on the scores. As described above, this may be done by ranking the products according to their respective scores for each of the health traits, selecting subsets of the ranked products for each health trait, assigning a recommendation to the products in each subset and then combining the recommendations for each health trait to produce an overall product recommendation for each product. The product recommendations may be chosen from a pre-defined set of product recommendations.

Step 704: Monitor the behaviour of the user by identifying periods when the user is in a sitting position or other sedentary state.

Step 705: Based on the behaviour of the user, modulate the product recommendation for at least of a subset of the products. The product recommendations may be modulated, for example, by assigning a different product recommendation from a pre-defined set of product recommendations. The subset may be determined based on the the products' scores for each health trait, e.g. a certain percentage of products which were "recommended" (i.e. "green") for a particular trait may be re-assigned to "maybe recommended" (i.e. "amber").

Step 706: Provide the modulated product recommendation to the user via a visual indicator, e.g. the light source 104 of the wristband 100.

It will be appreciated by the person of skill in the art that various modifications may be made to the above described embodiments without departing from the scope of the present invention.

The invention claimed is:

1. A wearable device comprising:
a memory configured to store product codes for consumable products and data indicating respective product recommendations or from which product recommendations can be derived;
a product code reader for reading product codes from products;
one or more inertial sensors for obtaining motion data for a wearer of the device;
a visual indicator for providing a visual indication of a product recommendation, using data stored in the memory, in response to a read product code; and
a processor configured to process the motion data to identify periods when the wearer is in a sitting position or other sedentary state, analyse the occurrence and durations of said periods, and modulate said recommendations accordingly for at least a subset of said product codes, whereby product recommendations change depending upon the identified periods.

2. A wearable device according to claim 1, wherein the processor is configured to modulate recommendations according to the wearer's behaviour determined by the processor for a pre-determined period, such as the same day.

3. A wearable device according to claim 1, wherein the processor is configured to
identify and maintain a count of periods when the wearer is in a sitting position or other sedentary state for a duration longer than a threshold duration, such as 10 minutes, 30 minutes or 60 minutes.

4. A wearable device according to claim 3, wherein the processor is configured to
ignore interruptions in which the user is not in a sitting position or other sedentary state for less than a pre-determined time when identifying said periods.

5. A wearable device according to claim 1, wherein said memory stores nutritional data for each product and said processor is configured to select said subset of product codes based on said nutritional data.

6. A wearable device according to claim 1, wherein each product recommendation has a first, recommended state and a second, not recommended state and said modulation changes a product recommendation between the first and the second state.

7. A wearable device according to claim 1, wherein said product recommendation has a first, recommended state, a second "maybe recommended" state and a third, not recommended state and said modulation changes the product recommendation between the first and the second state.

8. A wearable device according to claim 1, wherein the wearable device is a wrist-worn wearable device.

9. A wearable device according to claim 1, wherein said one or more inertial sensors comprises an accelerometer and/or a gyroscope.

10. A wearable device according to claim 1, wherein said product code reader is for reading a one-dimensional or two-dimensional barcode.

11. A wearable device according to claim 1, wherein said visual indicator provides said indications of the product recommendations by means of different coloured illuminations, for example red and green, or red, green and amber.

12. A method of providing recommendations in respect of consumable products to a wearer of a wearable device in order to improve the wearer's health, the method comprising:
storing, in a memory of the wearable device, product codes for products and data indicating respective product recommendations or from which product recommendations can be derived;
obtaining, from one or more inertial sensors of the wearable device, motion data for the wearer;
processing the motion data using a processor of the wearable device to identify periods when the wearer is in a sitting position or other sedentary state;
analysing the occurrence and durations of said periods using said processor;

reading a product code from a product using a product code reader of the wearable device;

in response to a read product code, using data stored in said memory to obtain a product recommendation;

modulating said product recommendation depending upon the wearer's sitting behaviour, or other sedentary behaviour, determined by the processor; and providing a visual indication of the modulated product recommendation using a visual indicator of the wearable device.

13. A method according to claim 12, further comprising selecting a subset of product codes for which the associated product recommendations are modulated.

14. A method according to claim 13, wherein selecting a subset of product codes for which product recommendations are modulated comprises selecting products codes based on nutritional information for the associated products.

15. A method according to claim 14, wherein selecting products codes based on nutritional information for the associated products comprises ranking the products based on the respective nutritional information for each product and selecting the subset by selecting products having a ranking higher than a pre-determined ranking.

16. A method according to claim 14, wherein the nutritional information comprises one or more of: calorific content, sugar content, carbohydrate content, saturated and/or unsaturated fat content, and salt content.

17. A method according to claim 12, wherein said data is derived from personalised data derived from personalised biological information obtained from an analysis of a biological sample provided by the wearer of the device.

* * * * *